United States Patent

Stiffler et al.

[11] Patent Number: 5,708,209
[45] Date of Patent: Jan. 13, 1998

[54] APPARATUS AND METHOD FOR ULTRASONIC PARTICLE DETECTION IN MOLTEN METAL

[75] Inventors: Richard C. Stiffler, Pittsburg; Ronald C. Wojnar, New Kensington, both of Pa.; Mark F. A. Warchol, Bettendorf, Iowa; Lawrence W. Cisko, Irwin, Pa.; John M. Urbanic, Pittsburgh, Pa.

[73] Assignee: Aluminum Company of America, Pittsburg, Pa.

[21] Appl. No.: 703,719

[22] Filed: Aug. 27, 1996

[51] Int. Cl.$^6$ ............ G01N 29/28; G01N 29/24
[52] U.S. Cl. ............ 73/644; 73/629; 73/632; 73/627
[58] Field of Search .......... 73/644, 573, 596, 73/597, 598, 599, 600, 628, 629, 632, 627

[56] References Cited

U.S. PATENT DOCUMENTS

| | | | |
|---|---|---|---|
| 3,444,726 | 5/1969 | Young et al. | 73/61 |
| 3,512,401 | 5/1970 | Thalmann | 73/67 |
| 4,175,442 | 11/1979 | Terry | 73/627 |
| 4,196,631 | 4/1980 | Deom et al. | 73/644 |
| 4,261,197 | 4/1981 | Mansfield | 73/61 |
| 4,287,755 | 9/1981 | Mansfield | 73/61 |
| 4,297,607 | 10/1981 | Lynnworth et al. | 73/642 |
| 4,510,812 | 4/1985 | Feng | 73/644 |
| 4,567,770 | 2/1986 | Rumbold et al. | 73/644 |
| 4,662,215 | 5/1987 | Eckert | 73/61 |
| 4,754,645 | 7/1988 | Piche et al. | 73/644 |
| 4,783,997 | 11/1988 | Lynnworth | 73/644 |
| 4,967,873 | 11/1990 | Hacchow et al. | 181/176 |
| 4,981,045 | 1/1991 | Mountford | 73/644 |
| 5,003,516 | 3/1991 | Sato et al. | 367/150 |
| 5,039,935 | 8/1991 | Hachey et al. | 324/71.4 |

*Primary Examiner*—Hezron E. Williams
*Assistant Examiner*—Nashmiya Ashraf
*Attorney, Agent, or Firm*—Tracey D. Beiriger

[57] ABSTRACT

An apparatus for conducting ultrasonic waves to and from a body of a molten material. The apparatus includes a buffer rod for transmitting ultrasonic waves to the molten metal, a second buffer rod for receiving ultrasonic waves from the molten metal, piezoelectric elements associated with each buffer rod, and cooling mechanisms for protecting the piezoelectric elements by maintaining the buffer rods at a prescribed rate of thermal equilibrium with the molten metal. The cooling mechanisms are configured so as to facilitate regulation of the air flow about the apparatus.

34 Claims, 3 Drawing Sheets

APPARATUS AND METHOD FOR ULTRASONIC PARTICLE DETECTION IN MOLTEN METAL

FIELD OF THE INVENTION

The present invention relates to an apparatus and a method for ultrasonic detection of inclusions in molten material.

BACKGROUND OF THE INVENTION

Because particulate inclusions in molten materials often have a detrimental effect on metal quality, considerable effort has been devoted in recent years to developing apparatus and methods for detecting such inclusions. The use of ultrasonic waves to inspect molten material is well known in the art, as disclosed, for example, by U.S. Pat. Nos. 4,981,045 to Mountford; 3,444,726 to Young et al; 4,261,197 to Mansfield; and 4,662,215 to Eckert.

Piezoelectric or electrostrictive transducers have the capability to both transmit and receive ultrasonic waves. Thus a single transducer may be used to perform both functions, or separate transducers may be used for transmitting and receiving. Both piezoelectric transducers and electrostrictive transducers can readily be made to handle high frequencies and low levels of power, and are accordingly well suited for molten material inspection methods.

As known in the art, a transducer can be coupled to the molten material using some type of buffer rod or acoustic wave guide which is typically in the form of a bar or rod. One end of such rod will be partially immersed in the molten material and is typically known as the "working tip," while the other end of the rod is coupled to the transducer. The rod serves to isolate the transducer from the high melt temperatures which could cause damage to the transducer. Also, the rod permits the introduction of a time delay between a transmitted pulse and echoes from inclusions located near where the pulse first enters the molten material.

It is desirable that an ideal acoustic wave guide or buffer rod material should have the following properties:

(a) The material should have a constant low acoustic energy attenuation over the range of working temperatures at the frequencies used.

(b) The material should be sound and homogeneous and free of internal flaws.

(c) The material should have good resistance to thermal and mechanical shock.

(d) The acoustic impedance of the material, i.e., the product of density and the velocity of sound, should be of the same order as the molten material.

(e) The material composition should facilitate wetting by the molten material.

(f) The material composition should be inert to the molten metal or does not cause contamination.

Various ultrasonic apparatus constructions consisting of a probe which contains some type of coupling medium have been disclosed by prior art, most of which was affected by one or more of the following problems: wetting did not occur at all or only after the passage of some substantial amount of time after the probe was initially immersed in the molten material; wetting did not occur after the probe was removed from the molten material, exposed to the atmosphere and cooled, and then immersed; at operating temperatures, the coupling medium attenuated the ultrasonic signals to an undesirable degree; or the probe material was not chemically stable in the molten material.

For example, the devices relying upon a probe of titanium metal have a short operating life when used to detect inclusions in molten aluminum because titanium is soluble in aluminum.

Another disadvantage of prior art devices is the need to provide a surface on the probe that is wettable by molten metal.

A further limitation of some prior art devices is the need to focus on a reflecting surface. Under production conditions, it is difficult to focus an ultrasonic beam and to maintain a reflective surface at a constant distance from the beam.

Another disadvantage of prior art devices is that they are fragile and difficult to assemble.

It is a principal objective of the present invention to obviate each of the above-mentioned disadvantages in the prior art.

Another objective of the invention is to provide an apparatus and method that can easily be adapted for various molten materials.

Yet another objective of the invention is to provide a probe that will not contaminate the molten material.

Still another objective of the invention is to provide a probe that is reusable.

A further objective and advantage of the invention is to provide an apparatus that is suitable for fabrication from conventional methods and materials.

One advantage of the preferred apparatus is that conventional ultrasonic instrumentation may be used.

A further advantage of the apparatus and method described herein is that the apparatus and method may be adapted for specific applications, for example, detecting material interfaces.

A still further advantage is that the apparatus is adapted to be readily moved from location to location including varying depths in the melt with no substantial interruption in the inspection process.

Yet another advantage is that the buffer rod is sufficiently wetted by the molten material.

SUMMARY OF THE INVENTION

In accordance with the present invention, there is provided an apparatus for conducting ultrasonic waves to and from a body comprising a molten material. The apparatus includes an acoustic wave guide or a buffer rod for transmitting ultrasonic waves to the molten metal, a second buffer rod for receiving ultrasonic waves from the molten metal, piezoelectric elements associated with each buffer rod, and cooling mechanisms for cooling the buffer rods and protecting the piezoelectric elements by maintaining the buffer rods within a prescribed temperature range. It is also possible, in the alternative, to provide an apparatus that includes only one buffer rod, piezoelectric element and cooling mechanism. In this case, the rod would both transmit and receive the ultrasonic waves.

The buffer rods comprise an upper end that is shaped to enhance air cooling, a cavity for holding a piezoelectric element, and an opposite lower end that is immersed in the molten material and is wettable by that molten material.

The buffer rods are preferably made substantially of the same material as the molten body. This minimizes the acoustic reflection between the buffer rods and the molten material. Further, the acoustic attenuation factor of the buffer rods can be minimized by using an alloy material exhibiting a fine grain structure with finely dispersed second phase particles. All acoustic attenuation and reflection factors are optimally as small as possible.

In preferred buffer rods used for analysis of molten aluminum, the buffer rods are made of pure aluminum or an aluminum alloy exhibiting a fine uniform microstructure. The ends of the buffer rods melt when the buffer rods are partially immersed in the molten aluminum. This allows wetting of the buffer rods by the molten aluminum which reduces the difference in the acoustic impedance between the buffer rods and the molten aluminum. Thus, good acoustic coupling results between the buffer rods and the molten aluminum. A single crystal aluminum or directionally solidified columnar grain aluminum may also be used for the buffer rods which minimizes acoustic attenuation of the transmitted or received signal.

Each buffer rod has its own cooling means comprising a sleeve that is located around a portion of the buffer rod, including that portion containing the piezoelectric element. Each cooling means also includes a shroud that has an inlet for compressed air to enter and that is positioned about the upper end of each buffer rod. The configuration of the sleeves and shrouds facilitate regulation of the air flow about the apparatus. Air flows throughout the annular space or channels created by the sleeves and shrouds to cool the buffer rod such that the apparatus and the molten body reach and maintain thermal equilibrium when the rods are partially immersed in the molten material. The cooling mechanisms maintain the lower end of the rod at a temperature cool enough such that approximately ¼-inch of each buffer rod which is immersed below the surface of the molten material and extends beyond the housing does not melt. The cooling mechanisms also assure that the piezoelectric elements will remain at a temperature at which they can operate effectively.

A preferred apparatus includes lithium niobate piezoelectric elements each having a center frequency between 1 and 25 MHz. An alternate preferred apparatus includes electrostrictive elements having a center frequency between 1 and 25 MHz.

The apparatus may further comprise a housing that contains at least a portion of both cooling sleeves. The apparatus during testing is positioned such that only the lower end of each buffer rod is disposed to contact the molten body. The housing minimizes the possibility of direct contact between the piezoelectric elements and the molten body and helps to maintain the piezoelectric elements at a temperature at which they can operate effectively. Further, the housing provides an area for the air to be controlled during circulation throughout the apparatus. Also, the housing provides a platform for properly locating the buffer rods with respect to each other. The housing is made of a material that is resistant to molten aluminum such as low carbon steel coated with a suitable protective material that is nonwettable by aluminum such as ceramic.

The present invention also provides a process for ultrasonically detecting particles in a moving molten material or metal stream or in a static molten body. This process utilizes the apparatus described above for carrying ultrasonic waves to and from a body comprising a molten material. The process comprises generating waves with a pulser/receiver system, transmitting such waves produced by a piezoelectric element through a first buffer rod acting as a coupling medium into the molten body, cooling the rod to maintain a thermal buffer between the associated piezoelectric element and molten body and receiving resultant signals through a second buffer rod with a piezoelectric element and interpreting those signals with a pulser/receiver system. The second buffer rod is also cooled to maintain a thermal buffer between the associated piezoelectric element and molten body. The process also includes, if necessary, cooling the lower end of the buffer rods to a temperature sufficient to freeze material from the molten body onto the immersed buffer rods. This allows the apparatus to be continually reused without replacing the buffer rods. In the alternative, a single buffer rod may be used to both transmit and receive signals.

DETAILED DESCRIPTION OF PREFERRED EMBODIMENTS

Figure 1:
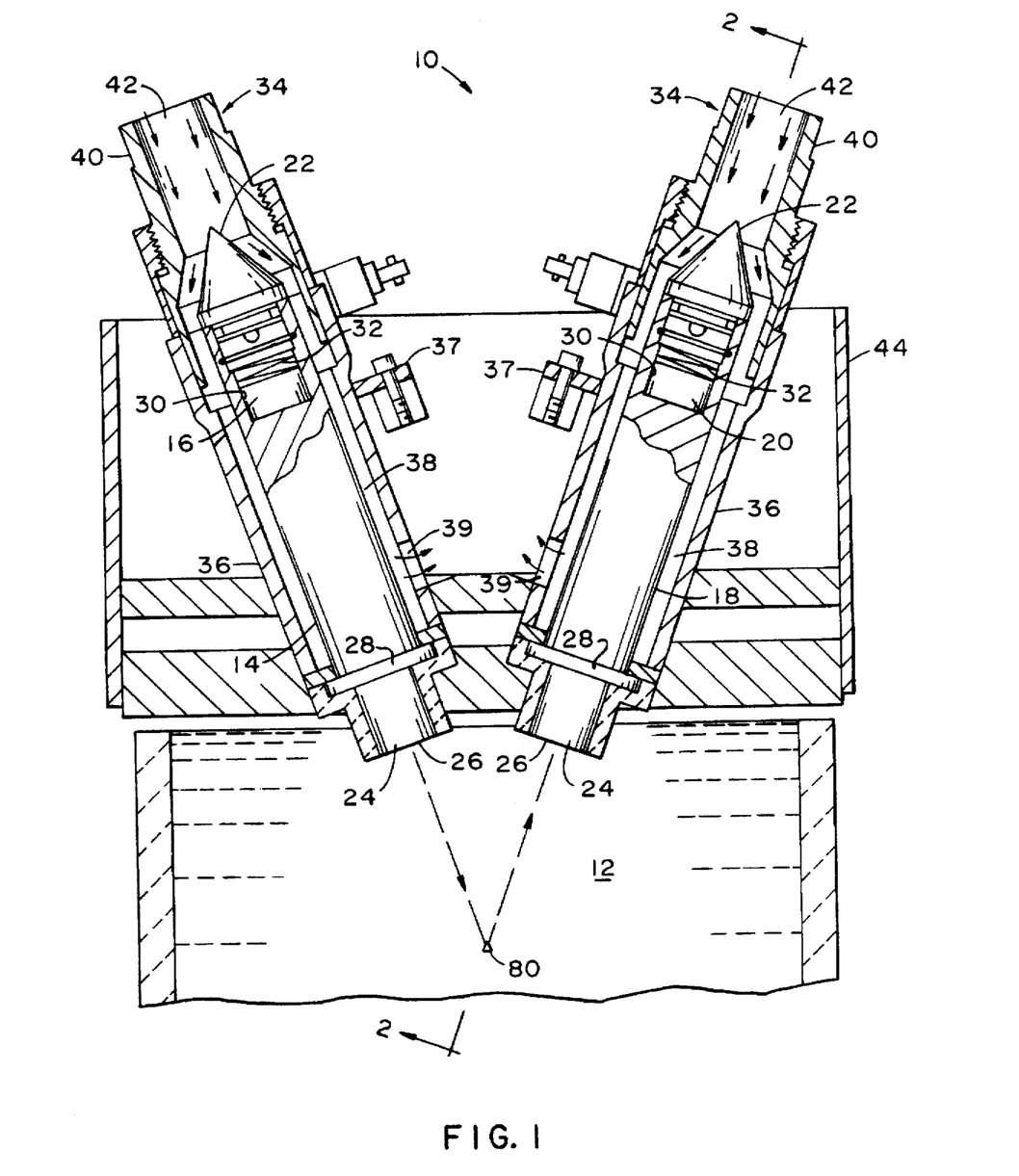
FIG. 1 is a schematic view of an apparatus for ultrasonic inspection of molten material, including the piezoelectric elements, buffer rods and cooling means of the present invention.

The apparatus 10 shown in FIG. 1 is used for detecting particulate inclusions in a body 12 comprising a molten material. While the particular apparatus and method described herein are intended for detection of particulate inclusions in molten aluminum and aluminum alloys, the invention is not limited to use solely with aluminum or for detection of only particulate inclusions. The present apparatus and method are also suitable for ultrasonic testing of other metals, including but not limited to bismuth, indium, lead, lithium, magnesium, tin, zinc, cobalt, copper, gold, iron, manganese, nickel, silver and their alloys.

The invention may also be applicable to ultrasonic testing of polymers or molten glasses, including silica glass, leaded silica glass, borosilicate glass, and flint glass. The greatest need for inclusion detection in glasses lies in optical quality glass manufacture. Further, the apparatus may be used, for example, to detect material interfaces.

Continuing with FIG. 1, the apparatus 10 includes a first buffer rod 14 and a first ultrasonic piezoelectric element 16 for transmitting ultrasonic waves to body 12, and a second buffer rod 18 and a second ultrasonic piezoelectric element 20 for receiving ultrasonic waves from body 12. The buffer rods 14 and 18 are positioned within the molten body 12 such that their projected center axes intersect each other before reaching the perimeter of the molten body. The rods are placed approximately 2 to 8 inches apart and at an angle 30 to 60 degrees relative to the horizontal plane of the molten body.

Buffer rods 14 and 18 each have an upper end 22 and an integral opposite lower end 24. The upper end 22 is shown as cone shaped in FIGS. 1 and 2 but may take on a variety of shapes that will influence air flow about the apparatus. Upper end 22 may be attached to the buffer rod, for example, via a light locational fit having O-ring retention. Lower ends 24 with faces 26 form working tips for the apparatus 10 which are exposed to and wetted by the molten material of body 12. The preferred buffer rods 14 and 18 are made of substantially the same material as the molten body 12. This minimizes the acoustic reflection at an interface between the buffer rods and the molten body 12. The acoustic reflection coefficient for ultrasonic waves between the piezoelectric elements 16 and 20 and the buffer rods 14 and 18, and between the buffer rods 14 and 18 and the molten body 12 should each be maintained as low as possible. It is possible, however, to achieve such desirable characteristics using a composite rod.

Figure 2:
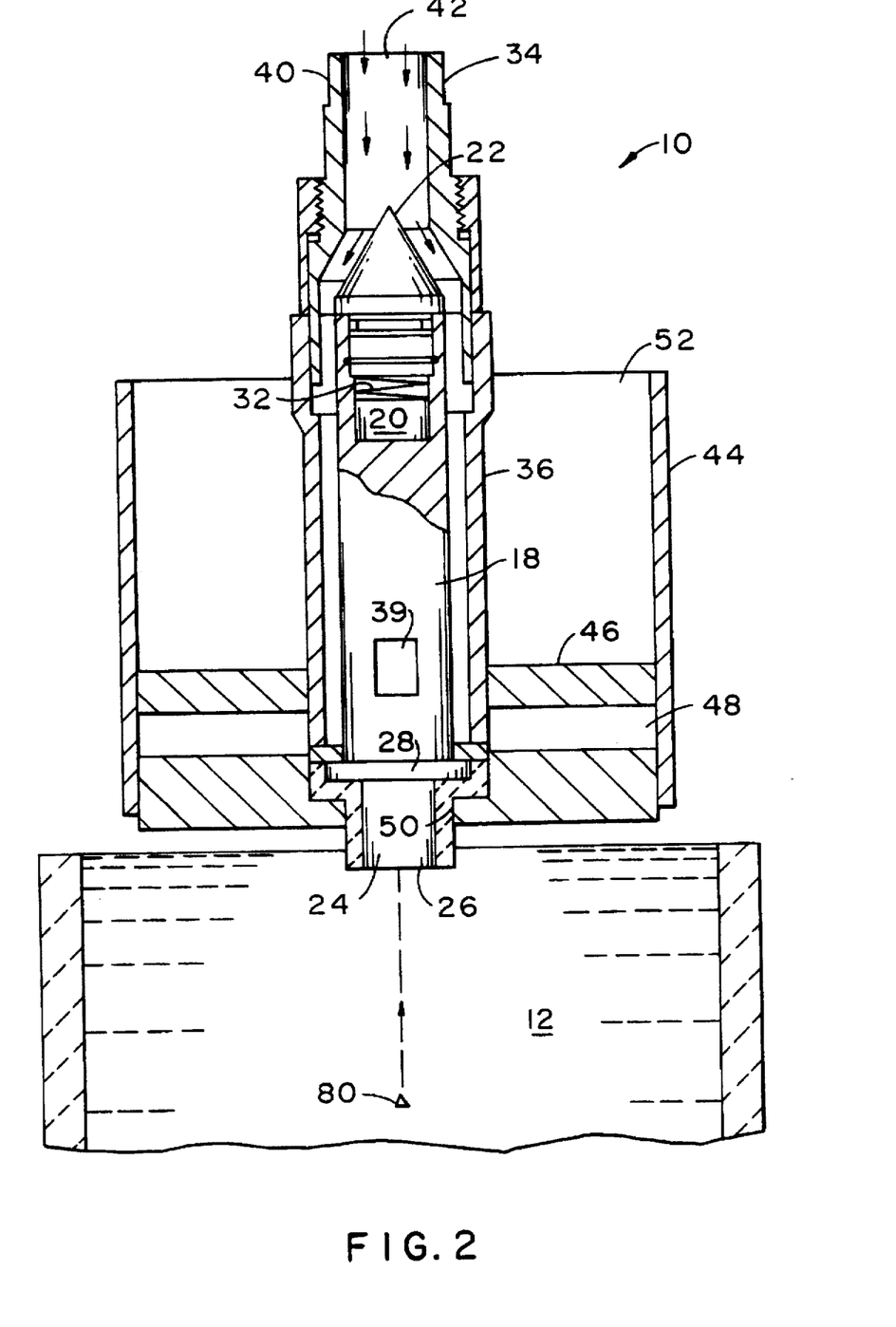
FIG. 2 is a sectional view of the apparatus of FIG. 1 taken along line 2—2 including a housing of the present invention.

To help minimize acoustical resistance, a suitable high temperature ultrasonic couplant (not shown) may be interposed between the upper ends 22 of the buffer rods 14 and 18 and the working contact surface of the piezoelectric element 16 and 20. For example, a high temperature ultrasonic couplant such as Sonotech, Inc.'s PYROGEL® couplant may be used.

Buffer rods 14 and 18 employed for analysis of aluminum, for example, preferably are made of pure aluminum or a fine grain aluminum. The aluminum buffer rods will melt when the buffer rods are partially immersed in the molten aluminum 12. This allows wetting of the buffer rods 14 and 18 and provides for an acoustic reflection of less than 15% between the aluminum buffer rods and the molten aluminum 12.

Between the upper ends 22 and the opposite second lower ends 24, each buffer rods 14 and 18 is approximately one inch in diameter. Upper ends 22 of the buffer rods 14 and 18 are cone shaped and act as air deflectors for apparatus 10 as described below. The opposite lower ends 24 of each buffer rod are about one inch in diameter and extend about one and one-half inch from faces 26 to collars or ledges 28 which are approximately two inches in diameter. Ledges 28 make up only about one-half of an inch of the length of each buffer rod 14 and 18. Approximately four inches from face 26 of each buffer rod 14 and 18 is a cavity 30 in which the transmitting piezoelectric element 16 and the receiving piezoelectric element 20 are respectively placed and secured.

Piezoelectric elements 16 and 20, being located in cavities 30 of buffer rods 14 and 18, respectively, send and receive ultrasonic waves through the buffer rods 14 and 18, which act as a coupling medium, into the molten body 12. Preferred piezoelectric elements 16 and 20 are lithium niobate. Such elements generate and receive ultrasonic waves having a center frequency of about 1 to 25 MHz in response to electrical stimuli. A particularly preferred operating frequency is about 5 MHz. Electrostrictive elements may be used rather than the preferred piezoelectric elements and will not adversely affect the operation of the apparatus. Operability of a typical piezoelectric element is limited by its Curie point temperature. For example, a quartz crystal must usually be operated at temperatures of 300° C. or less. However, lithium niobate crystals can operate at temperatures up to about 1300° C. Thus, it is important to cool the apparatus 10 such that the piezoelectric elements utilized will have their temperature maintained within the operating limit.

The piezoelectric elements 16 and 20 are conveniently mechanically secured in cavities 30 of buffer rods 14 and 18. A resilient means 32, such as a compression spring, relaxes stress between the piezoelectric element and the buffer rod resulting from expansion and contraction of the buffer rod. Such stress relaxation avoids breakage of a fragile piezoelectric element.

The apparatus 10 is provided with cooling means 34 which includes sleeves 36 and shrouds 40. Cooling means 34, preferably using air, extracts heat from the area of the piezoelectric elements 16 and 20 to protect the same from the high temperature of the molten material. The cooling means also extracts heat from the buffer rods 14 and 18. Other gases such as nitrogen, helium or argon may be used rather than air as the coolant. Liquid coolants such as water may be used depending on the material of the molten body. The sleeves 36 are preferably positioned around the upper ends 22 of the buffer rods 14 and 18 and extend to ledges 28 of the buffer rods. Ledges 28 aid in axially positioning the buffer rods. The cooling means 34 have the capacity to cool the apparatus 10 in a manner such that when the buffer rods 14 and 18 reach thermal equilibrium upon being partially immersed in the molten body 12, the piezoelectric elements 16 and 20 are maintained within their operating temperature range and at least a portion of the adjacent buffer rods 14 and 18 are maintained at a temperature below the melting point of the rod material.

A shroud 40 is placed about each cone-shaped upper end 22 of buffer rods 14 and 18. The lower ends of shrouds 40 are mechanically attached to sleeves 36 and clamps 37 and secure sleeves 36 to housing 44 which is described below. A particular preferred shroud is made of mild steel. Shroud 40 is provided an inlet 42 for compressed air to enter and be directed to channels 38 about the buffer rods.

The sleeves 36 form channels 38 through which air can be circulated to cool both the piezoelectric elements and the buffer rods. Outlets 39 are provided in the lower portion of the sleeves 36 to let air escape from channels 38 and circulate about the housing. A particularly preferred sleeve is principally made of mild steel.

The cooling means 34 operates to cool the buffer rods 14 and 18 such that at least ¼-inch of each buffer rod remains below the surface of the molten material and extends beyond the housing 44 (discussed below) without melting into or mixing with the material. By properly cooling the buffer rods through regulating air flow about the apparatus, the apparatus 10 and the molten material 12 will reach and maintain thermal equilibrium when the buffer rods 14 and 18 are partially immersed in the molten material. By using air, specifically compressed air, rather than a liquid such as water, for the coolant, the apparatus can safely be used without the potential of water mixing with the molten metal. This is especially advantageous when testing molten aluminum because of the hazardous reaction that takes place when water contacts molten aluminum. The cooling means 34 may be omitted entirely from the apparatus 10 if the apparatus is used for detection of inclusions in materials having low melting points such as bismuth, lithium or their alloys.

Other suitable materials for the sleeve and shroud include stainless steel, Invar, copper or aluminum. However, other materials may be used that exhibit the necessary physical properties.

As noted, the cooling means 34 must operate to extract heat at the buffer rods 14 and 18 such that approximately ¼-inch of the buffer rods remains below the surface of the molten material 12 and extends beyond the housing 44 (discussed below) without melting into or mixing with the material 12. It is also important that the cooling means 34 does not extract heat such that an appreciable amount of molten material 12 collects and solidifies on the lower ends 24 of the buffer rods 14 and 18 when the buffer rods are placed in contact with the molten material 12. Such solidified material can interfere with transmitted energy and scatter the ultrasonic waves in a manner that reduces the piezoelectric element's capability in providing critical information. A separation plate 46 may be provided within housing 44 (discussed below) that creates an air chamber 48 about the lower portion of the buffer rods. This air chamber helps to insulate the rods and prevents excess heat extraction so as to control such solidification and to maintain thermal equilibrium.

In a preferred apparatus 10 used for detecting inclusions in a molten aluminum body 12 and having aluminum buffer rods 14 and 18, the cooling means should maintain the piezoelectric elements 16 and 20 within their operating range and at least a portion of the buffer rods at a temperature below the melting temperature of the rod material. The portion maintained at such temperature should extend below the surface of the molten aluminum and beyond the housing 44 (discussed below) for approximately ¼-inch.

In a preferred apparatus 10 used for detecting inclusions in a molten aluminum body 12 and having aluminum buffer rods 14 and 18, the piezoelectric elements 16 and 20 and faces 26 of the lower ends 24 of the buffer rods should be separated by a distance of at least 4 inches. When it is desirable to maintain this distance as small as possible consistent with an acceptable thermal gradient, the distance can be increased in certain cases to avoid damaging the piezoelectric elements. In a preferred apparatus 10 described herein, the piezoelectric elements and the faces of the second end of the buffer rod are separated by a distance of about four inches.

Referring now to FIG. 2, the apparatus further comprises a housing 44 to contain buffer rods 14 and 18, piezoelectric elements 16 and 20 and cooling means 34 for protection from the high temperature molten body 12. The housing 44 preferably is elliptical and contains the buffer rods, the piezoelectric elements and the cooling means such that only the lower ends 24 of the buffer rods 14 and 18 are disposed to contact the molten body 12. More specifically, the housing 44 has openings 50 from which the lower ends 24 of the buffer rods 14 and 18 protrude and can contact the molten body 12 when the apparatus 10 is partially immersed in such body 12. The openings 50 in the housing 44 fit snugly around the buffer rods 14 and 18 so that the molten material 12 cannot penetrate the housing 44. The housing provides a platform for properly positioning the buffer rods within the molten body and with respect to each other. Housing 44 may take on various shapes other than cylindrical, depending on the circumstances under which the apparatus will be used. The housing shape, however, should not impede metal flow during use of the apparatus.

The housing 44 also has top openings 52 from which the upper ends 22 of buffer rods 14 and 18, along with a portion of the sleeves 36, protrude so that the shrouds 40 may be locked into place. As previously mentioned, a separation plate 46 may be included within the housing 44. The air chamber 48 created by such separation plate prevents the coolant from impinging on the bottom of housing 44 and over cooling of the buffer rods.

In the preferred apparatus, the housing 44 is made of a material that is resistant to molten aluminum such as low carbon steel coated with a protective ceramic material. The housing 44 minimizes the possibility of the molten body 12 contacting the piezoelectric elements while also providing additional insulation for the piezoelectric elements from the high melt temperatures of the molten body 12. The housing may also be made of a ceramic material.

The apparatus may also have a ceramic material 46, such as MARINITE®, placed around the ledges 28 and on the lower ends of the buffer rods to acoustically isolate each buffer rod. The ceramic material also provides a frangible interface to allow for the removal of used buffer rods from the housing. In certain instances, other insulating ceramic materials or high temperature polymers can be used about the buffer rods.

Figure 3:
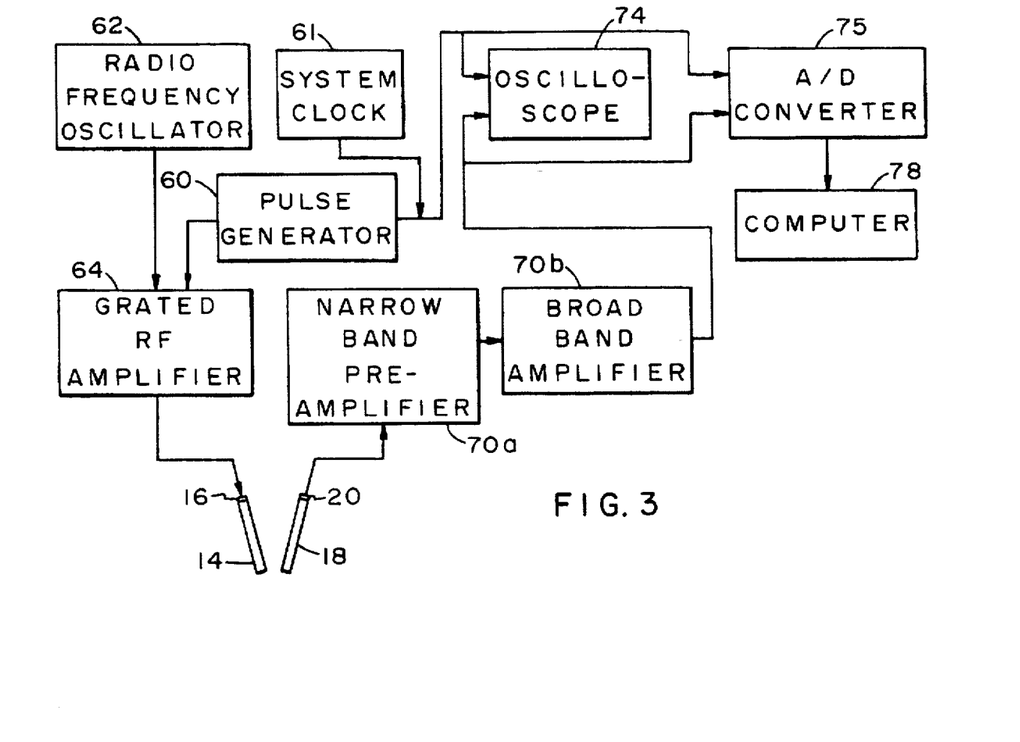
FIG. 3 is an exemplary circuit block diagram for operating the apparatus shown in FIGS. 1 and 2.

Referring to FIG. 3, the apparatus further comprises a pulse generator 60, a system clock 61, a radio frequency (RF) oscillator 62 generating alternating voltage of ultrasonic frequency, and a grated RF amplifier or modulator 64 receiving electrical pulses from the pulse generator 60 and the RF oscillator 62. The modulator 64 generates an alternating current voltage train of about 300 volts by passing a voltage of ultrasonic frequency only during the period that the modulator 64 is receiving a pulse from the pulse generator 60. This direct current voltage train energizes the piezoelectric element 16. Ultrasonic waves generated by the piezoelectric element 16 are transmitted through the buffer rod 14 and into the molten body 12.

In the preferred apparatus shown, the piezoelectric element 20 acts as a receiver for receiving wave trains from the molten body 12 through the buffer rod 18. This receiving element 20 then generates voltage trains in response to ultrasonic wave trains received from the molten body 12. The voltage trains so generated are sent to a narrow band tuned preamplifier 70a and then to a broad band amplifier 70b. These trains are then forwarded to oscilloscope 74 and to an A/D converter 75. A linear sweep circuit of oscilloscope 74 is synchronized with the pulse generator 60 by the system clock 61. The oscilloscope 74 has a spot that is deflected in one direction by the sweep circuit and deflected in a different direction by the voltage output from the broad band amplifier 70b. A computer 78, typically including mass storage and display, is used to collect data as it is received. The pulse generator 60, RF oscillator 62 and modulator 64 are referred to collectively as a "pulser." The amplifiers 70a and 70b are similarly called "receiver."

Ultrasonic waves generated by the piezoelectric element 16 are transmitted through the buffer rod 14 into the molten body 12. When these ultrasonic waves strike a suspended particle or particulate inclusion 80 in molten material 12, they are scattered back to the second buffer rod 18 and detected by piezoelectric element 20. The voltage trains are then displayed on the oscilloscope 74, digitized by analog to digital converter 75 and analyzed and recorded by computer 78. As previously noted, the rods are positioned within the molten body such that their projected center axes intersect each other before reaching the perimeter of the molten body. Such positioning facilitates properly directing the ultrasonic waves.

Figure 4:
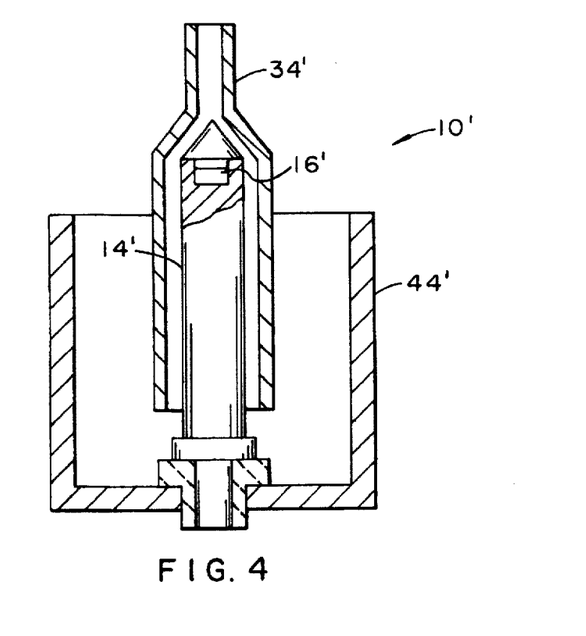
FIG. 4 is an alternate schematic embodiment of the present invention employing only a single buffer rod for carrying ultrasonic waves.

FIG. 4 shows an alternative embodiment of the invention. The apparatus 10' includes a single buffer rod 14' and piezoelectric element 16' shown in housing 44'. A cooling means 34' is used to maintain the buffer rod and piezoelectric element below a prescribed temperature. In this embodiment, the buffer rod 14' and piezoelectric element 16' transmit as well as receive ultrasonic waves.

The apparatus 10 is highly efficient at transmitting ultrasonic wave trains and hence can detect particles having an effective diameter of less than about 50 microns. Theoretically, the apparatus is capable of detecting particles as small as about 10 microns.

Having described the presently preferred embodiments, it is to be understood that the invention may be otherwise embodied within the scope of the appended claims.

What is claimed is:

1. An apparatus for conducting ultrasonic waves to and from a molten body and for sensing particles in the molten body, said apparatus comprising:

(a) an ultrasonic piezoelectric element;

9

(b) a buffer rod having a cavity for holding said piezoelectric element, said rod having an upper end shaped to influence flow of a coolant about the rod and an integral opposite lower end for contacting said molten body, said rod being made substantially of the same material as said molten body;

(c) a housing located around said piezoelectric element and rod for shielding said piezoelectric element and said rod from the molten body, said housing having an opening in which said lower end of the rod is disposed to contact the molten body;

(d) a shroud around said upper end of said buffer rod and serially connected to a sleeve disposed around said rod and said piezoelectric element, said shroud and said sleeve providing an internal cooling means for circulation of said coolant about said rod, said cooling means controlling the amount of cooling surface area to prevent substantial meltback of said rod and to prevent substantial buildup of molten body material on said rod such that said lower end of said rod extends approximately ¼-inch into said molten body beyond said housing when said apparatus is partially immersed in said body and said rod and said body reach thermal equilibrium; and (e) means for directing the coolant between said shroud and the upper end of said rod.

2. An apparatus according to claim 1 wherein the cavity for said piezoelectric element in said buffer rod is located between 3 and 6 inches from said opposite lower end of said rod.

3. An apparatus according to claim 1 wherein the diameter of said buffer rod between said upper end and said opposite lower end is approximately two inches and the diameter of said lower end is approximately one inch.

4. An apparatus according to claim 1 further comprising a ledge located about one and one-half inch from said opposite lower end of said rod and having a diameter of approximately 2 inches.

5. An apparatus according to claim 4 wherein a ceramic material is placed around said ledge and said lower end of said buffer rod to acoustically isolate said rod.

6. An apparatus according to claim 1 wherein the molten body is molten aluminum or aluminum alloy.

7. An apparatus according to claim 6 wherein said rod is made of aluminum or a fine grain aluminum alloy.

8. An apparatus according to claim 1 wherein the molten body is a metal selected from the group comprising aluminum, magnesium, tin, zinc or alloys thereof.

9. An apparatus according to claim 1 wherein the molten body is selected from the group comprising polymers or glass.

10. An apparatus according to claim 1 wherein the acoustic reflection between the rod and the molten body is less than 15%.

11. An apparatus according to claim 1 wherein said sleeve is principally made of mild steel.

12. An apparatus according to claim 1 wherein said coolant is gaseous.

13. An apparatus according to claim 12 wherein said gaseous coolant is air.

14. An apparatus according to claim 12 wherein said gaseous coolant is selected from the group comprising nitrogen, helium or argon.

15. An apparatus according to claim 1 wherein said upper end of said rod is cone shaped.

16. An apparatus according to claim 1 further comprising:

(d) a resilient means for relieving contact stress due to thermal expansion while maintaining contact between said buffer rod and said piezoelectric element.

10

17. An apparatus according to claim 16 wherein said resilient means comprises a spring.

18. A process for ultrasonically inspecting a molten body, said process comprising:

(a) fixedly placing an apparatus in contact with said molten body;

(b) generating ultrasonic waves with a pulser/receiver system of the apparatus;

(c) transmitting said waves and receiving resultant signals with a piezoelectric element through a buffer rod, said rod acting as a coupling medium between said piezoelectric element and said molten body, said rod having an upper end shaped to influence flow of a coolant about the rod and integral opposite lower end for contacting said molten body, said rod being made substantially of the same material as said molten body;

(d) controlling the amount of cooling to prevent substantial meltback of said rod and to prevent substantial buildup of molten body material on said rod such that said lower end of said rod extends approximately ¼-inch into said molten body beyond said housing when said apparatus is partially immersed in said body and when said rod and said body reach thermal equilibrium; and (e) interpreting the resultant signals with the pulser/receiver system.

19. The process of claim 18 wherein the molten body comprises molten aluminum and said rod is made of aluminum.

20. The process of claim 18 in which said step of transmitting said waves and receiving said signals includes transmitting said waves and receiving said signals with electrostrictive elements.

21. An apparatus according to claim 1 further comprising:

(f) a pulse generator;

(g) a system clock;

(h) a radio frequency oscillator for generating alternating voltage of ultrasonic frequency;

(i) a modulator for receiving electrical impulses from said pulse generator and said radio frequency oscillator, said modulator generating a voltage train by passing said voltage of ultrasonic frequency only during the period that said modulator is receiving a pulse from said pulse generator, said voltage train energizing said piezoelectric element;

(j) a means for said piezoelectric element to be actuated by vibration wave trains received from said body and generating voltage trains in response to said wave trains; and (k) an oscilloscope having a sweep circuit, said sweep circuit synchronized by said system clock with said pulse generator, said oscilloscope having a spot that is deflected in one direction by said sweep circuit and is deflected in a different direction by the voltage output from said piezoelectric element.

22. An apparatus for sensing particles in a molten body, said apparatus comprising:

(a) a first ultrasonic piezoelectric element;

(b) a second ultrasonic piezoelectric element;

(c) a first buffer rod for transmitting acoustic energy between said first piezoelectric element and said molten body, said first rod having a cavity for holding said first piezoelectric element, an upper end shaped to influence flow of coolant about the first rod and an integral opposite lower end for contacting said molten body;

(d) a second buffer rod for receiving acoustic energy between said second piezoelectric element and said molten body, said second rod having a cavity for holding said second piezoelectric element, said second rod having an upper end shaped to influence flow of said coolant about the second rod and an integral opposite lower end for contacting said molten body, said first and second buffer rods being made substantially of the same material as said molten body;

(e) a housing located around said piezoelectric elements and rods for shielding said piezoelectric elements and said rods from the molten body, said housing having openings in which said lower ends of the rods are disposed to contact the molten body;

(f) a first shroud around said upper end of said first rod and serially connected to a first sleeve disposed around said first rod and said first piezoelectric element, said first shroud and said first sleeve providing an internal first cooling means for circulation of said coolant about said first rod, said first cooling means controlling the amount of cooling sufficient to prevent substantial meltback of said first rod and to prevent substantial buildup of molten body material on said first rod such that said lower end of said first rod extends approximately ¼-inch into said molten body beyond said housing when said apparatus is partially immersed in said body and when said first rod and said body reach thermal equilibrium;

(g) a second shroud around said upper end of said second rod and serially connected to a second sleeve disposed around said second rod and said second piezoelectric element, said second shroud and said second sleeve providing an internal second cooling means for circulation of said coolant about said second rod, said second cooling means controlling the amount of cooling sufficient to prevent substantial meltback of said second rod and to prevent substantial buildup of molten body material on said second rod such that said lower end of said second rod extends approximately ¼-inch into said molten body beyond said housing when said apparatus is partially immersed in said body and when said second rod and said body reach thermal equilibrium; and (h) means for directing the coolant between said shrouds and the upper ends of said rods.

23. An apparatus according to claim 22 wherein said sleeves are principally made of mild steel.

24. An apparatus according to claim 22 wherein said coolant is gaseous.

25. An apparatus according to claim 24 wherein said gaseous coolant is air.

26. An apparatus according to claim 24 wherein said gaseous coolant is selected from the group comprising nitrogen, helium or argon.

27. An apparatus according to claim 22 wherein said upper ends of said rods are cone shaped.

28. An apparatus according to claim 22 further comprising a ledge located about one and one-half inch from each said opposite lower end of said first and said second rods and having a diameter of approximately 2 inches.

29. An apparatus according to claim 28 wherein a ceramic material is placed around said ledges and said lower ends of said buffer rods to acoustically isolate each said rod.

30. An apparatus according to claim 22 further comprising:

(f) a pulse generator;

(g) a system clock;

(h) a radio frequency oscillator for generating alternating voltage of ultrasonic frequency;

(i) a modulator for receiving electrical impulses from said pulse generator and said radio frequency oscillator, said modulator generating a voltage train by passing said voltage of ultrasonic frequency only during the period that said modulator is receiving a pulse from said pulse generator, said voltage train energizing said first piezoelectric element;

(j) a means for said second piezoelectric element to be actuated by vibration wave trains received from said body and generating voltage trains in response to said wave trains; and (k) an oscilloscope having a sweep circuit, said sweep circuit synchronized by said system clock with said pulse generator, said oscilloscope having a spot that is deflected in one direction by said sweep circuit and is deflected in a different direction by the voltage output from said second piezoelectric element.

31. An apparatus for sensing particles in a molten aluminum, said apparatus comprising:

(a) a first ultrasonic piezoelectric element;

(b) a second ultrasonic piezoelectric element;

(c) an aluminum or aluminum alloy first buffer rod for transmitting acoustic energy between said first piezoelectric element and said molten aluminum, said first rod having a cavity for holding said first piezoelectric element;

(d) an aluminum or aluminum alloy second buffer rod for receiving acoustic energy between said second piezoelectric element and said molten aluminum, said second rod having a cavity for holding said second piezoelectric element, each of said first rod and said second rod having a cone-shaped upper end to influence flow of air about the rods and an integral opposite lower end for contacting said molten aluminum, said cavity of each rod located between 3 and 6 inches from said opposite lower end of each said rod, each of said rods having a diameter between each said cone-shaped upper end and each said opposite lower end of approximately two inches and a diameter of each said opposite lower end of approximately one inch;

(e) a first shroud around said upper end of said first rod and serially connected to a first sleeve disposed around said first rod and said first piezoelectric element, said first shroud and said first sleeve providing an internal first cooling means for circulation of said air about said first rod, said first cooling means cooling said lower end of said first rod such that said apparatus reaches and maintains thermal equilibrium with said molten aluminum with substantially little melting of said first rod in the molten aluminum when said apparatus is partially immersed in said molten aluminum;

(f) a second shroud around said upper end of said second rod and serially connected to a second sleeve disposed around said second rod and said second piezoelectric element, said second shroud and said second sleeve providing an internal second cooling means for circulation of said air about said second rod, said second cooling means cooling said lower end of said second rod such that said apparatus reaches and maintains thermal equilibrium with said molten aluminum with substantially little melting of said second rod in the molten aluminum when said apparatus is partially immersed in said molten aluminum;

(g) means for directing the air between said shrouds and the upper ends of said rods;

(h) a housing located around said piezoelectric elements and rods for shielding said piezoelectric elements and said rods from the molten aluminum, said housing having openings in which said lower ends of the rods are disposed to contact the molten aluminum, said first and second cooling means controlling the amount of cooling sufficient to prevent substantial meltback of said rods and to prevent substantial buildup of molten aluminum on said rods such that said lower end of said rods extends approximately ¼-inch into said molten aluminum beyond said housing when said apparatus is partially immersed in said molten aluminum and when said rods and said molten aluminum reach thermal equilibrium; and (i) a pulser/receiver system for operating said piezoelectric elements, said system adapted to generate; receive and interpret signals between said piezoelectric elements and the molten aluminum.

32. An apparatus according to claim 31 wherein said sleeves are principally made of mild steel.

33. An apparatus according to claim 31 further comprising a ledge located about one and one-half inch from each said opposite lower end of said first and second rods and having a diameter of approximately 2 inches.

34. An apparatus according to claim 33 wherein a ceramic material is placed around said ledges and said lower ends of said buffer rods to acoustically isolate each said rod.

* * * * *

UNITED STATES PATENT AND TRADEMARK OFFICE
CERTIFICATE OF CORRECTION

PATENT NO.    : 5,708,209
DATED         : January 13, 1998
INVENTOR(S)   : Richard C. Stiffler; Ronald C. Wojnar; Mark F.A. Warchol;
                Lawrence W. Cisko; John M. Urbanic It is certified that error appears in the above-indentified patent and that said Letters Patent is hereby corrected as shown below:

Col. 9, line 17     Change "surface area" to --sufficient--.

Signed and Sealed this

Twenty-fourth Day of March, 1998

Attest:

BRUCE LEHMAN

*Attesting Officer*     Commissioner of Patents and Trademarks